(12) United States Patent
DeBusk et al.

(10) Patent No.: US 9,827,064 B2
(45) Date of Patent: Nov. 28, 2017

(54) ELECTROMAGNETIC ABSORBING MATERIAL IN OPENING OF SHIELDED ENCLOSURE

(71) Applicant: DeRoyal Industries, Inc., Powell, TN (US)

(72) Inventors: Brian C. DeBusk, Knoxville, TN (US); Joe L. Smith, Powell, TN (US); Mark E. McKnight, Knoxville, TN (US); Haben M. Jemal, Knoxville, TN (US); Mary E. Kaylor, Chattanooga, TN (US); Gerald T. Griffith, Knoxville, TN (US); Nicholas Poker, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 62 days.

(21) Appl. No.: 15/012,067

(22) Filed: Feb. 1, 2016

(65) Prior Publication Data

US 2017/0215980 A1    Aug. 3, 2017

(51) Int. Cl.
| | |
|---|---|
| *A61B 50/36* | (2016.01) |
| *B65F 1/14* | (2006.01) |
| *B65F 1/16* | (2006.01) |
| *H05K 9/00* | (2006.01) |
| *A61B 50/30* | (2016.01) |

(52) U.S. Cl.
CPC ............ *A61B 50/36* (2016.02); *B65F 1/1431* (2013.01); *B65F 1/1607* (2013.01); *H05K 9/005* (2013.01); *A61B 2050/3006* (2016.02)

(58) Field of Classification Search
CPC ...... A47G 29/122; A47G 29/14; A47G 29/30; A61B 50/36; A61B 2050/3006; B65F 1/1431; B65F 1/1607; B65F 1/06; B65F 1/08; B65F 1/10; H05K 9/005; G06K 19/07327
USPC ............... 232/45, 43.1, 43.2, 44; 220/908.3; 340/10.1, 572.8, 572.7; 343/841; 361/800
See application file for complete search history.

(56) References Cited

U.S. PATENT DOCUMENTS

| | | | | |
|---|---|---|---|---|
| 816,989 | A * | 4/1906 | Moler et al. ............. | B65F 1/06 220/495.1 |
| 1,380,252 | A * | 5/1921 | Richardson ............... | B65F 1/08 220/641 |
| 2,125,122 | A * | 7/1938 | Mongiello ................ | B65F 1/08 220/23.89 |

(Continued)

*Primary Examiner* — William Miller
(74) *Attorney, Agent, or Firm* — Luedeka Neely Group PC

(57) ABSTRACT

A shielded enclosure receives REID-tagged packaging from consumed medical items. The enclosure includes a housing and a lid. An opening in the lid receives the packaging into an internal space. A chute surrounds the opening and extends downward into the internal space. The chute has front, left, right, and rear walls. A hood attached to the lid surrounds the opening. An aperture in the hood allows passage of the packaging into the lid opening. The hood includes rear, right, left, and top walls. RF absorbing material covers inside surfaces of the chute and hood, including a front panel on the chute front wall, a rear panel on the hood rear wall and the chute rear wall, a left side panel on the hood left side wall and the chute left side wall, a right side panel on the hood right side wall and the chute right side wall, and a top panel on the hood top.

8 Claims, 4 Drawing Sheets

(56) References Cited

U.S. PATENT DOCUMENTS

| | | | |
|---|---|---|---|
| 6,588,656 B2 * | 7/2003 | Cox | A47G 29/16 |
| | | | 232/47 |
| 7,036,719 B1 * | 5/2006 | Helphrey | A47G 29/124 |
| | | | 232/30 |
| 2007/0109130 A1 | 5/2007 | Edenfield | |
| 2010/0213086 A1 | 8/2010 | Emond et al. | |
| 2016/0285171 A1 * | 9/2016 | Moylan | H01Q 17/007 |

* cited by examiner (section A-A in *FIG. 1*)

ELECTROMAGNETIC ABSORBING MATERIAL IN OPENING OF SHIELDED ENCLOSURE

FIELD

This invention relates to the field of RF shielded enclosures. More particularly, this invention relates to an RF absorbing material disposed in and around an opening of an RF shielded enclosure.

BACKGROUND

In hospitals and other medical facilities, Radio Frequency Identification (RFID) tags are attached to medical items to provide the following general functions: (1) identifying medical items or other resources that enter a room or other space in a medical facility; (2) determining where those medical items or other resources came from; and (3) determining whether those medical items or other resources were consumed during a medical procedure performed in the room or space. Generally, each medical item pulled for use during a particular medical procedure includes an MD tag affixed to the item's outer packaging. These RFID tags contain appropriate inventory information regarding each item as maintained in the inventory control system of the medical facility. Generally, each individual item can be tracked through use of the RFID tags and appropriate REID reader technology.

When scanning RFID tags of medical items consumed during a medical procedure, it is important to avoid unintentional "stray reads" of tags on items that are not consumed during the procedure. To avoid stray reads, some prior systems implement short range RFID readers operating in low-frequency (LF) or high-frequency (HF) bands that read tags at distances of less than about 1 meter. When using such systems, the user must bring the RFID tag into close proximity with the sensing antenna.

One disadvantage of the LF and HF systems is their relatively low data transfer rate. For inventory control purposes that call for higher data transfer rates, it is desirable to use ultrahigh frequency (UHF) RFID readers. However, due to the longer-range sensitivity of UHF systems, stray reads can become a problem when such systems are used in environments that are not completely electromagnetically sealed, such as an enclosure that has an opening to allow materials to pass into or out of the enclosure.

What is needed, therefore, is a shielded enclosure that, though not being completely electromagnetically sealed due to the necessity of an access opening, prevents stray RFID signals from entering the opening and being detected inside the enclosure.

SUMMARY

In some embodiments described herein, an Operating Room (OR) or other procedure room has a shielded enclosure with an RFID antenna disposed inside. Preferably, a waste bin or other such receptacle is disposed in the shielded enclosure, and an opening is provided in the top of the enclosure to allow items to be dropped into the waste bin. The shielded enclosure and an RFID reader connected to the antennas may be located near where sterile medical supplies are typically opened by the circulating nurse or other OR/procedure room personnel responsible for setting up the OR/procedure room for each procedure.

Once the packaging of a medical supply is opened, that item is considered to be consumed because the packaging has been compromised and it cannot be re-stocked. As the packaging of a medical supply item having an RFID tag is opened, the packaging is dropped through the opening in the shielded enclosure and into the waste bin inside the enclosure and the reader reads the RFID tag on that packaging. The RFID reader is connected to a data collection interface, such as an Operating Room Information System (ORIS) computer terminal, a tablet computer or smart phone, and the consumption information for each item is logged.

Such systems provide an accurate way to track supply utilization that does not require additional data input steps from OR/procedure room personnel. Simply throwing the discarded packaging into a waste bin, which is normal procedure, allows for the RAID tagged supplies to be registered as consumed. For such systems to perform properly, the shielded enclosure and the associated RFID antenna and reader should be configured so as to only sense RFID tags that are inside the enclosure and not to sense RFID tags outside the enclosure.

To prevent electromagnetic signals entering the shielded enclosure through the opening, preferred embodiments described herein provide RF absorbing material on specific surfaces surrounding the opening. The RF absorbing material attenuates RF energy that is incident on and reflected from surfaces, thereby eliminating any reflective path into the interior of the shielded enclosure.

In one preferred embodiment, a shielded enclosure is provided for receiving discarded packaging from medical items consumed during performance of a medical procedure. The packaging of the consumed medical items has RFID tags attached thereto. The shielded enclosure includes an internal space for receiving the packaging and a housing that at least partially encloses the internal space. A lid is attached to an upper portion of the housing such that it is disposed over and covers the internal space. The lid has an opening that allows passage of the discarded packaging into the internal space. A chute surrounds the opening in the lid and extends downward from the lid into the internal space. The chute includes a chute front wall, a chute left side wall, a chute right side wall, and a chute rear wall. A hood is attached to the lid and is disposed above and at least partially surrounds the opening in the lid. The hood has an aperture that allows passage of the discarded packaging into the opening in the lid. The hood includes a hood rear wall, a hood right side wall, a hood left side wall, and a hood top.

RF absorbing material is disposed above the opening in the lid and covers inside surfaces of the chute and the hood. In a preferred embodiment, the RF absorbing material includes an RF absorber front panel attached to the front wall of the chute, an RE absorber rear panel attached to the hood rear wall and the chute rear wall, an RE absorber left side panel attached to the hood left side wall and the chute left side wall, an RF absorber right side panel attached to the hood right side wall and the chute right side wall, and an RF absorber top panel attached to the hood top.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
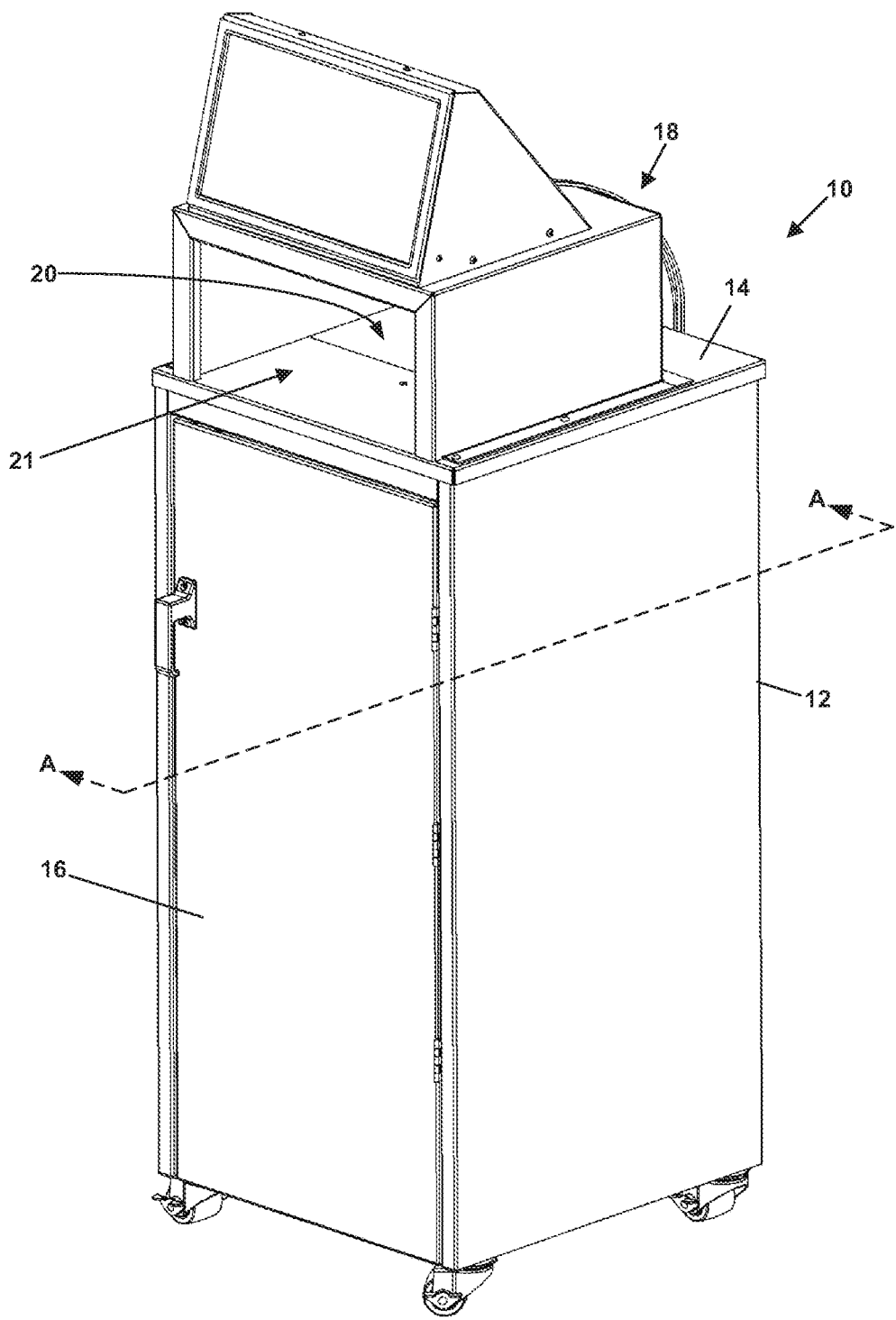
FIG. 1 depicts a shielded enclosure according to an embodiment of the invention.
Figure 2:
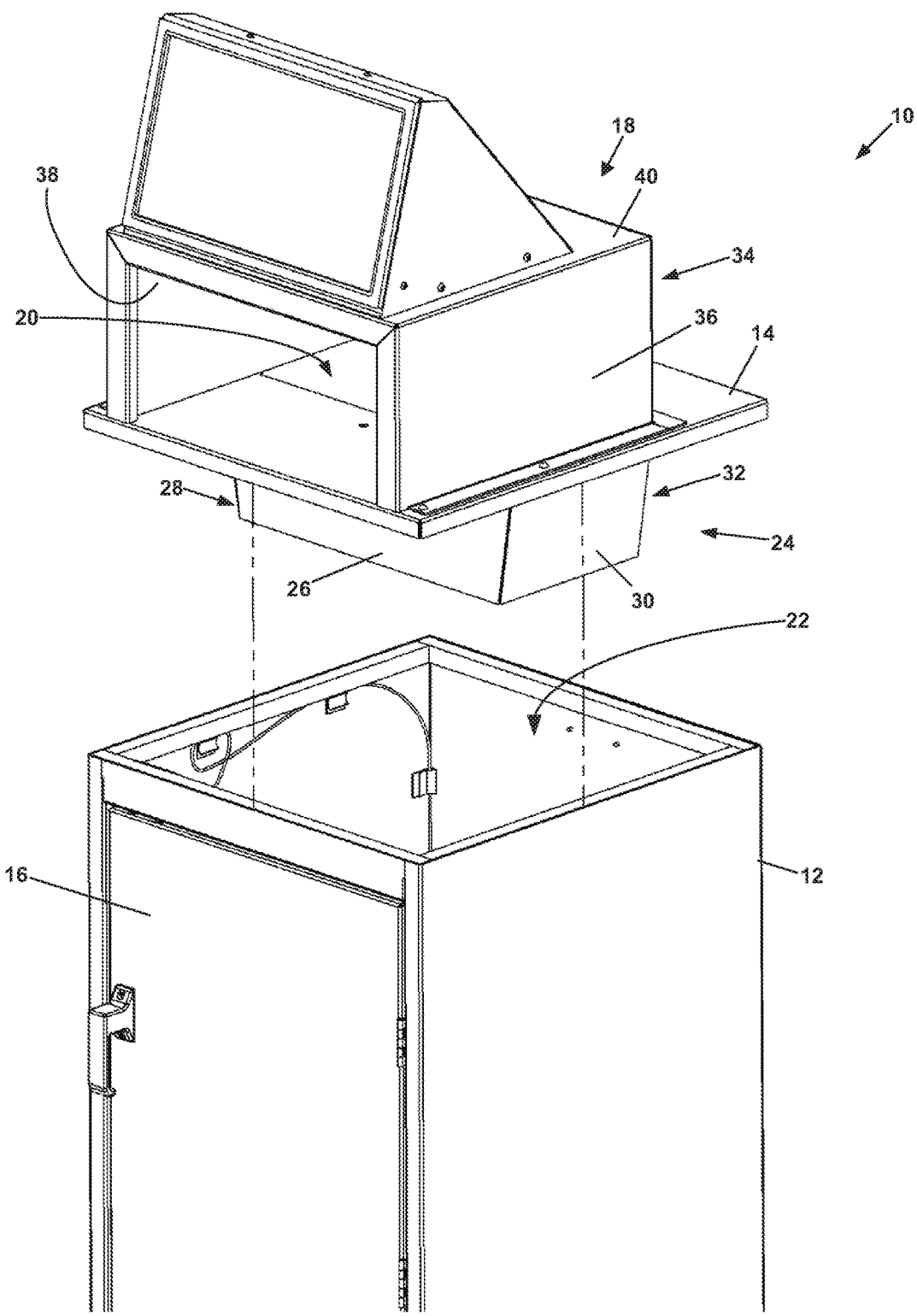
FIG. 2 depicts the shielded enclosure with its lid removed according to an embodiment of the invention.

FIGS. 1 and 2 depict a shielded enclosure 10 for receiving discarded packaging of medical items that were consumed during a medical procedure. The enclosure 10 includes a housing portion 12 having an internal space 22 that is large enough to receive a waste bin. In a preferred embodiment, the enclosure 10 is constructed from 0.080 inch thick sheet aluminum supported by 0.75×0.75 inch square aluminum tubing. The outside dimensions of the preferred embodiment are 23.5×22.0×40.75 inches.

The top of the housing portion 12 is covered by an aluminum lid 14. An opening 20 is provided in the lid 14 that is large enough to receive the packaging from which medical items have been removed. In the preferred embodiment, the opening 20 is a 6.75×13.75 inch rectangle. An aluminum hood 18 is provided over the opening 20 to help prevent RF signals from escaping the enclosure 10. As shown in FIG. 1, the hood 18 has a front aperture that allows passage of the discarded packaging into the opening 20 in the lid 14. As shown in FIG. 2, the lid 14 includes an aluminum chute 24 that surrounds the opening 20. A waste bin (not shown) may be positioned below the opening 20 to catch packaging that is deposited in the opening 20.

In some embodiments, the lid 14 and the hood 18 are integrally formed as part of the housing portion 12. In some embodiments, the lid 14 and hood 18 are removable and may be detached from the housing portion 12.

In a preferred embodiment, a hinged door 16 large enough to receive the waste bin is provided in a front sidewall of the housing 12. The door 16 is preferably 29.5×39.25 inch, and includes a handle/latch for securing the door in a closed position. The enclosure 10 is considered to be substantially shielded when the door 16 is closed.

As the term is used herein, "shielded" means that the enclosure 10 is designed to prevent an RFID antenna disposed inside the enclosure 10 from receiving RFID signals from RFID tags located outside the enclosure 10 at a signal-to-noise ratio high enough to trigger detection of those outside RFID tags. For purposes of this disclosure, "shielded" does not mean that absolutely all RF energy is blocked from entering the enclosure, as this would require unnecessary levels of shielding.

As shown in FIG. 2, the chute 24 has a front wall 26, a left side wall 28, a right side wall 30, and a rear wall 32. The hood 18 has a rear wall 34, a right side wall 36, a left side wall 38, and a top 40.

Figure 3:
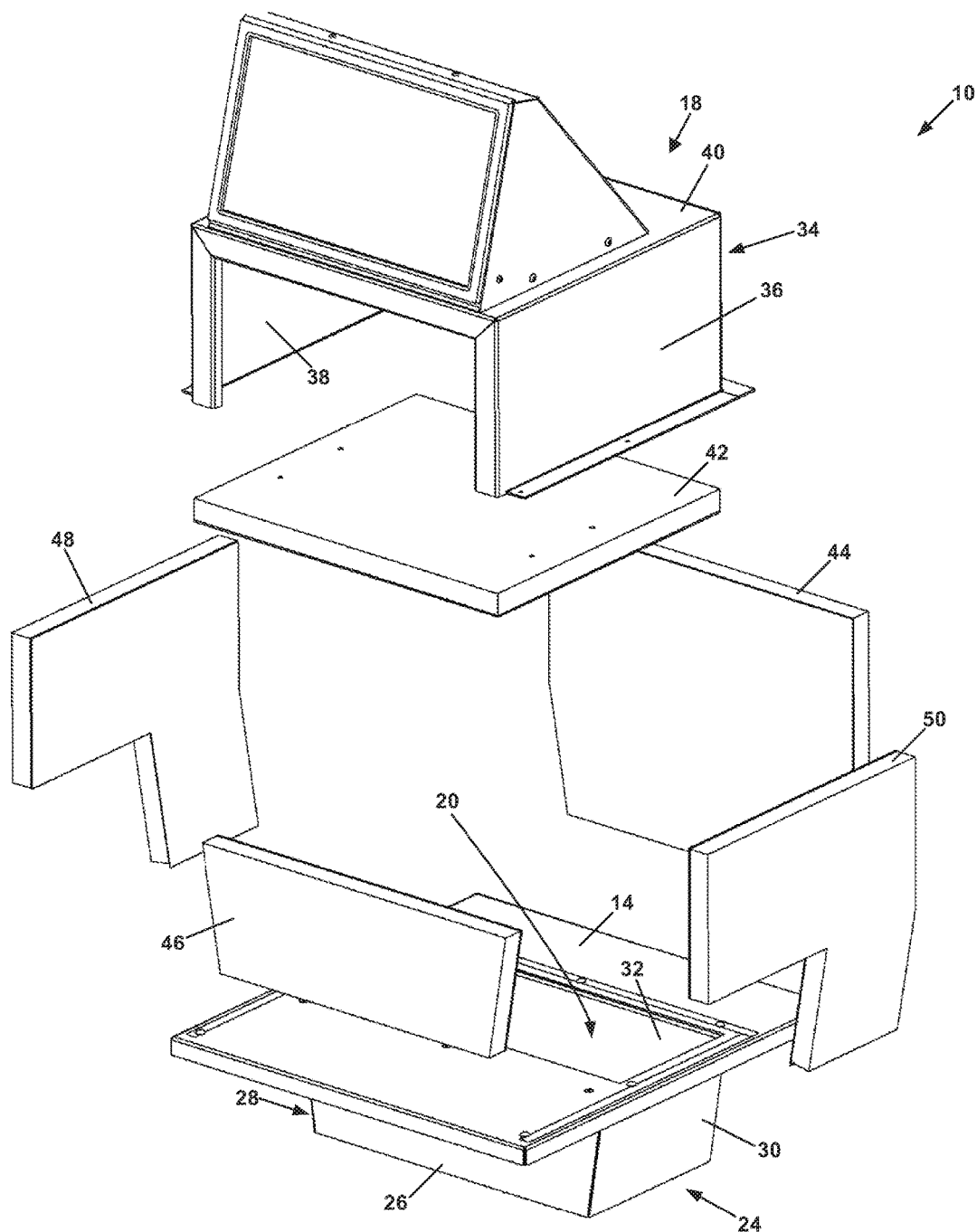
FIG. 3 depicts an exploded view of the shielded enclosure's hood, lid with opening, chute, and RE absorber panels according to an embodiment of the invention.

FIG. 3 is an exploded view with the hood 18 separated from the lid 14. This view depicts five panels of RF absorbing material that attach to interior surfaces of the hood 18 and the chute 24. In a preferred embodiment, the RF absorber panels are constructed from one-inch thick sheets of a Lossy Foam Absorber product from MAST Technologies of San Diego, Calif. (Part No. MF22-0009-00), which introduce about −45 dB of insertion loss to a signal passing through, or about −90 dB total insertion loss to a once-reflected signal. The five panels include:

a front panel 46 that attaches to the inner surface of the front wall 26 of the chute 24;

a rear panel 44 that attaches to the inner surface of the rear wall 32 of the chute 24 and the rear wall 34 of the hood 18;

a left side panel 48 that attaches to the inner surface of the left side wall 28 of the chute 24 and the left side wall 38 of the hood;

a right side panel 50 that attaches to the inner surface of the right side wall 30 of the chute 24 and the right side wall 36 of the hood; and a top panel 42 that attaches to the inner surface of the top 40 of the hood.

In an alternative embodiment, the RF absorbing panels 42-50 are formed from an RF isolation coating, such as an ME-500 coating product manufactured by MWT Materials Inc. of Passaic, N.J. In this embodiment, the RF absorbing panels 42-50 are integrally formed as a continuous coating on the inside surfaces of the hood 18, the opening 20, and the chute 24.

The inventors have determined that placement of the RF absorbing panels 42-50 on the interior surfaces of the hood 18, opening 20 and chute 24 effectively prevents RF signals in the operating frequency range used for RFID tags from entering or exiting the enclosure 10 at detectable levels, thereby eliminating stray readings of RFID tags that are outside the enclosure 10.

Figure 4:
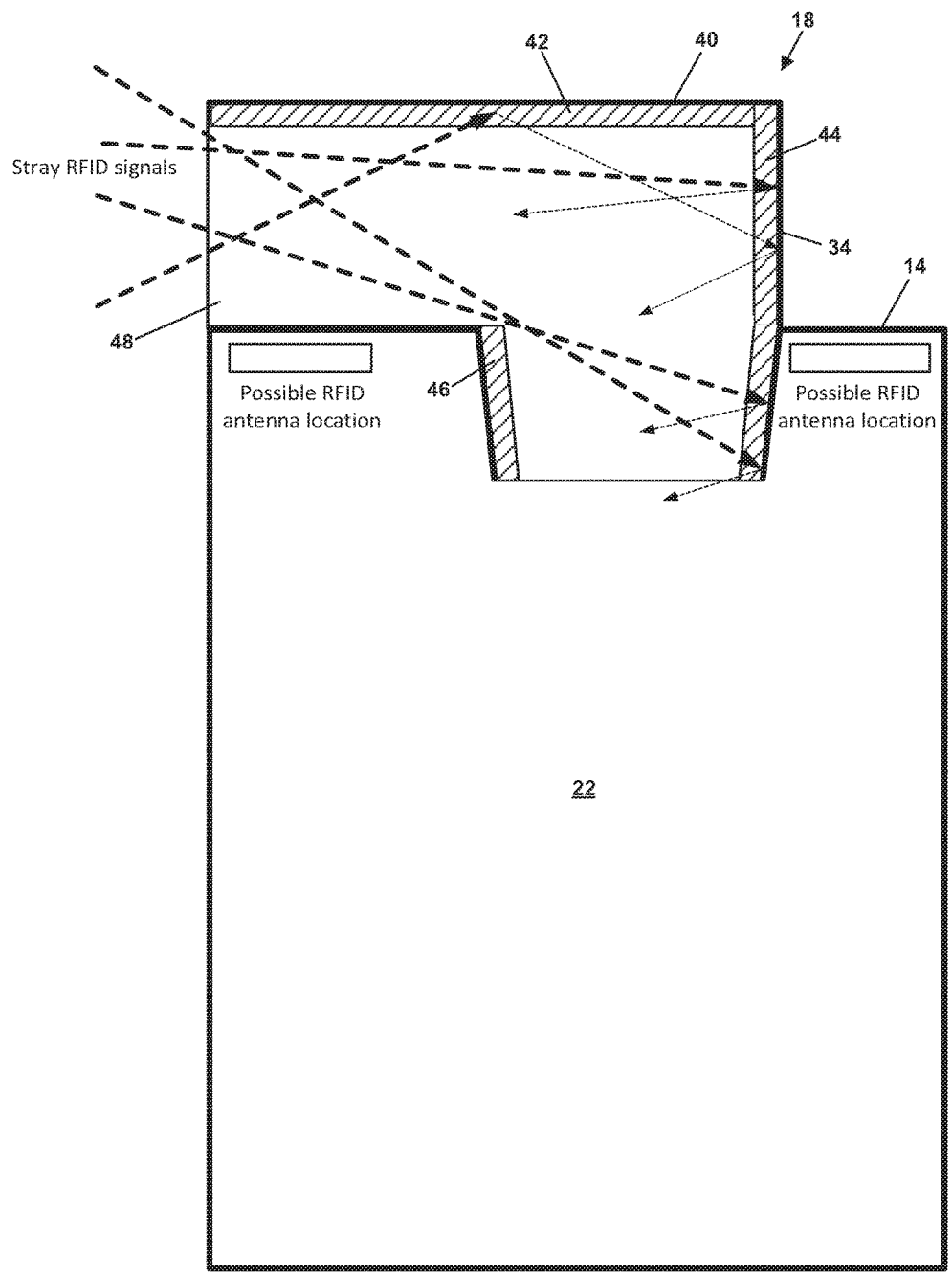
FIG. 4 depicts a vertical cross-section view of the shielded enclosure with representation of the attenuation of stray RFID signals.

As illustrated in the cross-section view of FIG. 4, stray RFID signals entering or exiting the hood 18 from any angle in the vertical plane will encounter at least one of the panels 42, 44 or 46. A signal passing through any one of the panels, reflected from the metal surface behind the panel, and passing again through the panel, encounters about −90 dB total loss, which effectively renders the signal undetectable to an RFID reader. The same is true for signals entering or exiting the hood from any angle in the horizontal plane, which will encounter at least one of the panels 44, 48 and 50.

Thus, preferred embodiments of the invention (1) attenuate RFID signals that originate from RFID antennas inside the enclosure so as to reduce interference with RFID systems in the vicinity outside the enclosure, and (2) attenuate RFID signals that originate from RFID antennas outside the enclosure so as to reduce interference with the reading of RFID tags inside the enclosure.

Those skilled in the art will appreciate that embodiments described herein have application beyond the medical field. The shielded enclosure may be used in any application wherein the enclosure cannot be completely electromagnetically sealed due to the necessity of an access opening, but wherein it is important to prevent stray RFID signals from passing through the opening. Thus, the invention is not limited only to the medical field or to use only with medical items consumed during a medical procedure. Embodiments of the shielded enclosure described herein may be used with any type of RFID-tagged item.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A shielded enclosure for receiving discarded packaging from medical items consumed during performance of a medical procedure, wherein the packaging has RFID tags disposed therein or thereon, the shielded enclosure comprising:
an internal space for receiving the packaging of the medical items;
a housing that at least partially encloses the internal space, the housing comprising:
an upper portion that is disposed over and covers the internal space, the upper portion having:
an opening that allows passage of the discarded packaging into the internal space;
a chute extending downward from the opening into the internal space, the chute surrounding the opening;
a hood that is disposed over and at least partially surrounds the opening, the hood having an aperture that allows passage of the discarded packaging into the opening; and
RF absorbing material at least partially covering one or more inside surfaces of the chute and hood,
wherein the RF absorbing material is configured in such a manner that radio frequency signals entering the aperture are attenuated to levels that are substantially undetectable within the internal space, and radio frequency signals exiting the aperture are attenuated to levels that are substantially undetectable outside the shielded enclosure.

2. The shielded enclosure of claim 1 further comprising:
the chute comprising:
a chute front wall;
a chute left side wall;
a chute right side wall; and
a chute rear wall; and
the RF absorbing material comprising:
an RF absorber front panel attached to the chute front wall;
an RF absorber rear panel attached to the chute rear wall;
an RF absorber left side panel attached to the chute left side wall; and
an RF absorber right side panel attached to the chute right side wall.

3. The shielded enclosure of claim 2 further comprising:
the hood comprising:
a hood rear wall;
a hood right side wall;
a hood left side wall; and
a hood top; and
the RF absorbing material comprising:
the RF absorber rear panel attached to the hood rear wall and the chute rear wall;
the RF absorber left side panel attached to the hood left side wall and the chute left side wall;
the RF absorber right side panel attached to the hood right side wall and the chute right side wall; and
an RF absorber top panel attached to the hood top.

4. The shielded enclosure of claim 1 further comprising:
the hood comprising:
a hood rear wall;
a hood right side wall;
a hood left side wall; and
a hood top; and
the RF absorbing material comprising:
an RF absorber rear panel attached to the hood rear wall;
an RF absorber left side panel attached to the hood left side wall;
an RF absorber right side panel attached to the hood right side wall; and
an RF absorber top panel attached to the hood top.

5. The shielded enclosure of claim 1 further comprising a door in a sidewall of the housing, the door covering an opening that is large enough to accommodate a waste bin for receiving the discarded packaging.

6. The shielded enclosure of claim 1 wherein the RF absorbing material comprises an RF isolation coating.

7. A shielded enclosure for receiving discarded packaging from medical items consumed during performance of a medical procedure, wherein the packaging has RFID tags disposed therein or thereon, the shielded enclosure comprising:
an internal space for receiving the packaging of the medical items;
a housing that at least partially encloses the internal space;
a lid attached to an upper portion of the housing, the lid disposed over and covering the internal space, the lid having an opening that allows passage of the discarded packaging into the internal space;
a chute surrounding the opening in the lid and extending downward from the lid into the internal space, the chute comprising:
a chute front wall;
a chute left side wall;
a chute right side wall; and
a chute rear wall; and
a hood attached to the lid and disposed above and at least partially surrounding the opening in the lid, the hood having an aperture that allows passage of the discarded packaging into the opening in the lid, the hood comprising:
a hood rear wall;
a hood right side wall;
a hood left side wall; and
a hood top; and
RF absorbing material disposed above the opening in the lid and covering inside surfaces of the chute and the hood, the RF absorbing material comprising:
an RF absorber front panel attached to the chute front wall;
an RF absorber rear panel attached to the hood rear wall and the chute rear wall;
an RF absorber left side panel attached to the hood left side wall and the chute left side wall;
an RF absorber right side panel attached to the hood right side wall and the chute right side wall; and
an RF absorber top panel attached to the hood top,
wherein the lid is attached to the housing and the hood is attached to the lid in such a manner that radio frequency signals emanated from RFID tags disposed outside the shielded enclosure are attenuated to levels that are substantially undetectable within the internal space.

8. A shielded enclosure for receiving packaging removed from one or more items, the packaging having one or more RFID tags disposed therein or thereon, the shielded enclosure comprising:
an internal space for receiving the packaging; and a housing that at least partially encloses the internal space, the housing comprising:
  an upper portion that is disposed over and covers the internal space, the upper portion having:
    an opening that allows passage of the packaging into the internal space;
    a chute extending downward from the opening into the internal space, the chute surrounding the opening;
    a hood that is disposed over and at least partially surrounds the opening, the hood having an aperture that allows passage of the packaging into the opening; and
    RF absorbing material at least partially covering inside surfaces of the chute and at least partially covering inside surfaces of the hood,
  wherein the RF absorbing material is configured in such a manner that radio frequency signals emanated from RFID tags disposed outside the shielded enclosure are attenuated to levels that are substantially undetectable within the internal space, and radio frequency signals emanated from one or more RFID antennas disposed inside the shielded enclosure are attenuated to levels that are substantially undetectable outside the shielded enclosure.

* * * * *